United States Patent [19]

Sakurada et al.

[11] 4,237,886
[45] Dec. 9, 1980

[54] ELECTRODE TO BE USED IN CONTACT WITH A LIVING BODY

[75] Inventors: Isoji Sakurada, Kanuma; Tadasu Kawashima, Utsunomiya, both of Japan

[73] Assignees: Sony Corporation; Natsuo Uchiyama, both of Tokyo, Japan

[21] Appl. No.: 892,200

[22] Filed: Mar. 31, 1978

[30] Foreign Application Priority Data

Apr. 2, 1977 [JP] Japan ................................. 52-37821
Jan. 31, 1978 [JP] Japan ............................. 53-10506[U]

[51] Int. Cl.³ ............................................. A61B 17/36
[52] U.S. Cl. ............................... 128/303.13; 128/798; 252/511
[58] Field of Search .................. 128/303.13, 2.06 E, 128/2.1 E, 404, 410, 411, 416-418, DIG. 4, 639-641, 644, 783, 798, 802, 803; 252/510, 511

[56] References Cited

U.S. PATENT DOCUMENTS

| | | | |
|---|---|---|---|
| 3,911,906 | 10/1975 | Reinhold, Jr. | 128/2.06 E |
| 3,972,329 | 8/1976 | Kaufman | 128/2.06 E |
| 3,993,049 | 11/1976 | Kater | 128/2.06 E |
| 4,016,869 | 4/1977 | Reichenberger | 128/2.1 E |
| 4,066,078 | 1/1978 | Berg | 128/2.06 E |
| 4,088,133 | 5/1978 | Twentier | 128/303.13 |
| 4,125,110 | 11/1978 | Hymes | 128/2.06 E |

FOREIGN PATENT DOCUMENTS

| | | | |
|---|---|---|---|
| 13888 | 4/1970 | Australia | 128/418 |
| 122258 | 2/1972 | Denmark | 128/2.06 B |
| 50-18702 | 2/1975 | Japan | 252/511 |

*Primary Examiner*—Lee S. Cohen
*Attorney, Agent, or Firm*—Lewis H. Eslinger; Alvin Sinderbrand

[57] ABSTRACT

An electrode, or grounding pad for contact with a living body comprises a conductive substrate of a textile having conductive fibers, a conductive adhesive layer containing carbon fibers for contacting the surface of the living body and being affixed to the conductive substrate, and an electrical connection to the conductive substrate.

15 Claims, 8 Drawing Figures

ELECTRODE TO BE USED IN CONTACT WITH A LIVING BODY

BACKGROUND OF THE INVENTION

1. Field of the Invention

This invention relates to electrodes to be used in contact with a living body such as the human body, and more particularly to electrodes to be used as grounding pads opposite active surgical electrodes during surgery.

2. Description of the Prior Art

The conventional electrode or "grounding pad" is contacted with the thigh, back or other portions of the human body at a location opposite an active surgical electrode or electro-surgical pencil with blade. An electric current is passed from the active electrode to the grounding pad through the human body to provide a cutting or coagulating action at selected locations.

In the conventional electrode or grounding pad, a gauze containing a physiological saline solution is affixed on a metal plate of lead, stainless steel or the like, having a lead wire extending therefrom. The electrode is contacted with the human body through the gauze. Unfortunately, such conventional construction of the electrode gives rise to various disadvantages. For example, due to poor flexibility of the electrode, contact with the curved surfaces of a human body can become uneven or the saline solution may dry with extended usage, both of which conditions can result in uneven current density over the contact area and the danger of burns. In addition, miniaturization of such an electrode, for application to limited areas, is difficult. Further, problems with sanitization of the electrode can develop.

Another known construction of the conventional electrode or grounding pad, is of a so-called conductive jelly type, wherein a sponge containing conductive jelly is affixed to an inner surface of a sponge-like substrate to form the electrode. Contact with the human body is effected through the conductive jelly, while the sponge-like substrate is affixed to the human body through adhesive material coated on the marginal portion of the inner surface thereof. A lead wire is connected with the sponge containing the conductive jelly. Although an opposed electrode or grounding pad of this type is at least initially relatively well contacted with the human body so that unevenness of electric current density is relatively decreased, there is still a danger of burns being suffered due to uneven contact when the conductive jelly is dried after being used for a long time. In addition, special steps are required for sanitizing the electrode and preventing water evaporation therefrom, such as, enclosing the electrode in a sanitary bag or sak. Such additional procedure adds complication and expense to the production and use of this type of electrode.

In still another known type of electrode or grounding pad, a metal foil of aluminum or the like is directly contacted with the human body, and the metal foil is attached to a substrate of larger size than the foil, and the substrate is affixed to the human body through adhesive material coated on the marginal portion of the inner surface thereof. Unfortunately, electrodes of this type are liable to wrinkle due to poor flexibility of the metal foil. As a result, contact with the human body is not uniform and uneven current distribution results with the danger of burns occurring. Also, this type of electrode is not suitable for surgical operations on children because of its relatively large size.

In a conventional conductive adhesive, metal particles, such as, of copper or silver, are dispersed in a resin, and this adhesive can be applied to a tape. Unfortunately, the specific resistance of such an adhesive is liable to become uneven or unstable, because it is higher than that of the conductive particles contained in the resin and the particles are not surely contacted with the electric conductor. For this reason, when such a conductive adhesive tape is attached to a living body and to the lead wire, a relatively low resistance value cannot be obtained unless the adhesive tape is attached under strong pressure to cause the metal particles to be forcibly exposed on the surface of the adhesive layer to produce good conductivity. Accordingly, when the conventional adhesive is applied as an opposed electrode or grounding pad for an electric-surgical pencil, or the like, there is a danger of causing a concentration of an electric current density if the pressure on the adhesive is weak or uneven.

OBJECTS AND SUMMARY OF THE INVENTION

Accordingly, it is an object of the present invention to provide an electrode, or grounding pad, for contact with a living body, and which forms uniform contact with the latter to provide even current distribution across the area of contact.

Another object of the invention is to provide an electrode or grounding pad which will not dry out with extended use and thereby cause an uneven current distribution and the danger of burns.

Still another object of the invention is to provide an electrode or grounding pad, as aforesaid, which is flexible and can conform to various surface shapes on a living body.

A further object of the invention is to provide an electrode or grounding pad, as aforesaid, which can be formed in a small size for contact with limited surface areas.

It is a further object of the invention to provide an electrode or grounding pad, as aforesaid, which ensures good current distribution over the surface area of the electrode by providing sufficient electrical contact between the electrode and the lead wire affixed thereto.

It is a still further object of the invention to provide an electrode or grounding pad, as aforesaid, having good mechanical strength.

In accordance with an aspect of this invention, an electrode or grounding pad for electrically contacting a living body comprises a conductive substrate made of a textile having conductive fibers, a conductive adhesive layer for contacting a surface of the living body, said adhesive layer being affixed to said conductive substrate and containing carbon fibers, and means forming an electrical connection to said conductive substrate.

In accordance with a feature of the invention, the adhesive layer includes a mixture of carbon fibers and a resin, wherein the carbon fibers may have a length of 0.2 to 6mm and a diameter of 1 to 20 $\mu$m and are continued in said adhesive layer in an amount ranging from about 2 to 30% by weight relative to the remainder of the adhesive layer.

In accordance with another feature of the invention, both the substrate and the adhesive layer have a specific resistance, or resistivity, of less than 100$\Omega$ cm., and the conductive substrate has a thickness of 50 to 100 $\mu$m which the adhesive layer has a thickness of 25 to 200 μm.

In accordance with another feature of the invention, the adhesive layer includes a resin having a base polymer, a major part of which consists of an acrylic or methacrylic acid ester of an alcohol having 1 to 8 carbon atoms in its molecule, and a minor part of which consists of a vinyl compound having a crosslinkable functional group. In one embodiment, the acrylic or methacrylic acid ester is substituted by another vinyl compound in an amount of less than 20 parts by weight of the other vinyl compound for each 100 parts by weight of the acrylic or methacrylic acid ester. In another embodiment, the vinyl compounds are copolymerized in the base polymer in the range of 0.25 to 3.0 parts by weight of said vinyl compounds for each 100 parts by weight of the total amount of the base polymer.

In accordance with a further feature of the invention, the means forming an electrical connection to the conductive substrate includes a cylindrical member having a flanged end and penetrating said adhesive layer and said substrate with said flanged end being at the side of said adhesive layer, and an interconnection member affixed to the other end of said cylindrical member and being in electrical contact with the conductive substrate. Such interconnection member may be soldered to the conductive substrate and crimped on the cylinderical member so as to be affixed to the latter. The cylinderical member may desirably have an insulating cover of the flanged end thereof to prevent electrical contact between the cylindrical member and the surface of the living body. The electrode may further have flexible insulating material affixed to the conductive substrate on the side opposite the adhesive layer.

The above, and other objects, features and advantages of the invention, will be apparent in the following detailed description of illustrative embodiments to be read in connection with the accompanying drawings.

DETAILED DESCRIPTION OF PREFERRED EMBODIMENTS

Before proceeding with the description of the invention, reference will be made to FIG. 1 in which a conventional electrode of the conductive jelly type is shown to comprise a sponge-like substrate 1, an adhesive layer 2, an insulating frame 3 affixed to the sponge-like substrate 1 through the adhesive layer 2, a stainless steel plate 4 located inside the frame 3, a conductive lower electrode element 6 which is inserted from the lower side of the substrate 1 into a hole 5 formed therein and in the plate 4, a conductive upper electrode element 7 which is mechanically united with an extruded portion 6a of element 6, and a doubling or back-up plate 9. To unite the upper electrode element 7 with the lower electrode element 6, the element 7 is placed over the extruded portion 6a of element 6 and crimped, as at 8, against the element 6. The frame 3 is filled with a foam sponge 10 containing conductive jelly which extends over an area larger than that occupied by plate 4. The sponge 10 and the conductive jelly therein is contacted with a flanged end 6b of lower element 6 and with the stainless steel plate 4.

Figure 1:
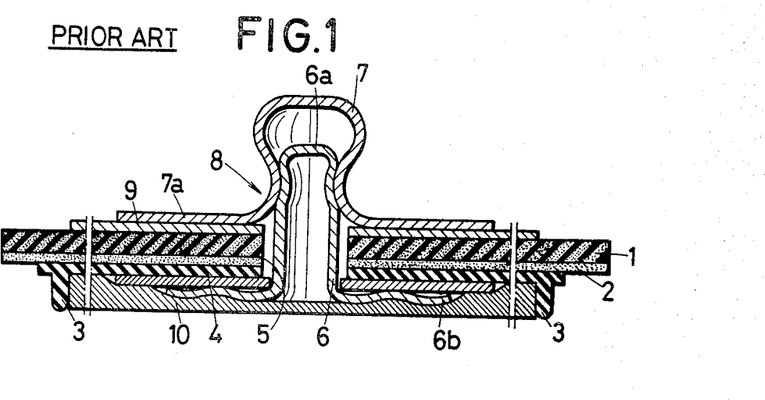
FIG. 1 is a cross-sectional view of a conventional electrode, or grounding pad.

In the electrode of FIG. 1, the stainless steel plate 4 has a larger surface area than the flanged end 6b of the lower electrode element 6. The plate 4 thereby is able to reduce the electrical resistance of the electrode and spread the electric current over a larger surface area to prevent concentrations thereof. Unfortunately, the sponge 10 is insufficient for maintaining a suitable electric contact and becomes relatively bulky because it must be formed relatively thick in consideration of the volume decrease that occurs upon drying of the conductive jelly. Electrical contact between the elements 6 and 7 is also limited as these elements are only electrically connected with each other at the crimped region 8. The conventional electrode of FIG. 1 additionally suffers from poor mechanical strength due to poor attachment of its element 7 to the substrate 1. Further, there is a danger of burns occurring due to the drying of the conductive jelly when used for a long time.

Figure 2:
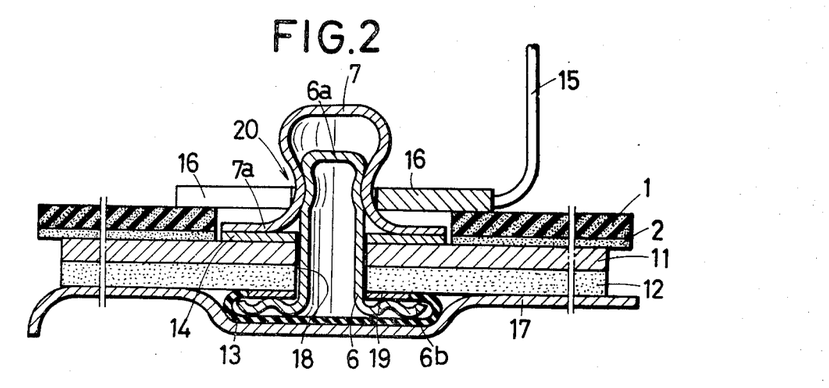
FIG. 2 is a cross-sectional view of an electrode or grounding pad, according to the present invention.

Referring now to FIG. 2, it will be seen that an electrode or grounding pad 20 according to this invention is there illustrated to generally comprise a conductive substrate 11, a conductive adhesive layer 12, upper and lower electrode elements 7 and 6, respectively, a ring-shaped solder layer 14, a washer 19, a sponge-like substrate 1, an adhesive layer 2, a lead wire 15 with a terminal plate 16, and an insulating cover or cap 13.

The electrode or grounding pad 2, of FIG. 2 is particularly characterized by the conductive substrate 11 and the conductive adhesive layer 12. The conductive substrate 11 includes a textile having conductive fibers of suitable composition and the conductive adhesive layer 12 is affixed to the conductive substrate and contains carbon fibers for providing electrical conductivity therethrough. Further details of the conductive substrate 11 and adhesive layer 12 are given below.

The conductive substrate 11 and the conductive adhesive layer 12 have a penetrating hole 18 therethrough. The lower electrode element 6 extends through the penetrating hole 18 and has a flanged end 6b at the lower, or contact, side of adhesive layer 12. The washer 19 is located around the lower electrode element 6 and between the flanged end 6b and the conductive adhesive layer 12. The insulating cap or cover 13 is located over the flanged end 6b of electrode 6 for preventing direct electrical contact between the lower electrode element 6 and the surface to be contacted. The insulating cap 13 may be in the form of a steel plate covered by a polyvinyl chloride film.

The upper portion of lower electrode element 6 forms an extruded and exposed portion 6a which is located within a central, downwardly opening socket in the upper electrode element 7. As with the conventional electrode shown in FIG. 1, in the electrode 20 of FIG. 2, the upper electrode element 7 is affixed to the lower electrode element 6 by crimping in the area 8 of the upper electrode element 7.

Figure 6:
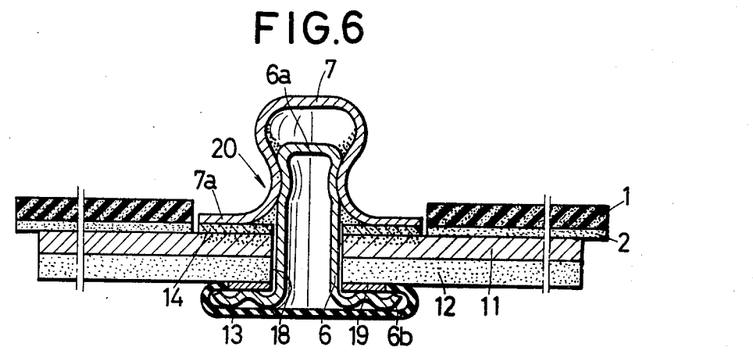
FIG. 6 is a cross-sectional view similar to FIG. 2, but showing solder material impregnated into a conductive substrate.

The upper electrode element 7 is formed with a flange portion 7a extending radially out from the central socket of element 7. A ring-shaped solder layer 14 is located between flange portion 7a and conductive substrate 11 around lower electrode element 6. In the construction of the electrode 20, the ring-shaped solder layer 14 may initially be in the form of a washer of solder material which is first assembled into the electrode and then melted, thereby becoming affixed to and forming good electrical contact between the upper electrode element 7, the lower electrode element 6 and the conductive substrate 11. As a result, it is possible to unite the solder material of the solder washer 14 with the electrode element 7 and to impregnate the solder material into the conductive substrate 11 for achieving an anchoring effect. The shading on FIG. 6 illustrates the resulting solder dispersal achieved when the upper element 7 is crimped to attach elements 6 and 7, right after or while being heated to melt the solder. The solder washer 14 may comprise a solder material having a melting point of more than 60° C. Alternatively, the layer 14 may be formed by a conductive paint or a solder paste which is printed or otherwise applied on conductive substrate 11 before the electrode elements 6 and 7 are united. In this case, no further heating is required because the anchoring effect on the conductive substrate 11 is achieved when printing the conductive paint or the solder paste. However, when solder paste is used, it is preferable to improve the contact between the particles of the solder paste by the subsequent heating thereof.

Figure 5:
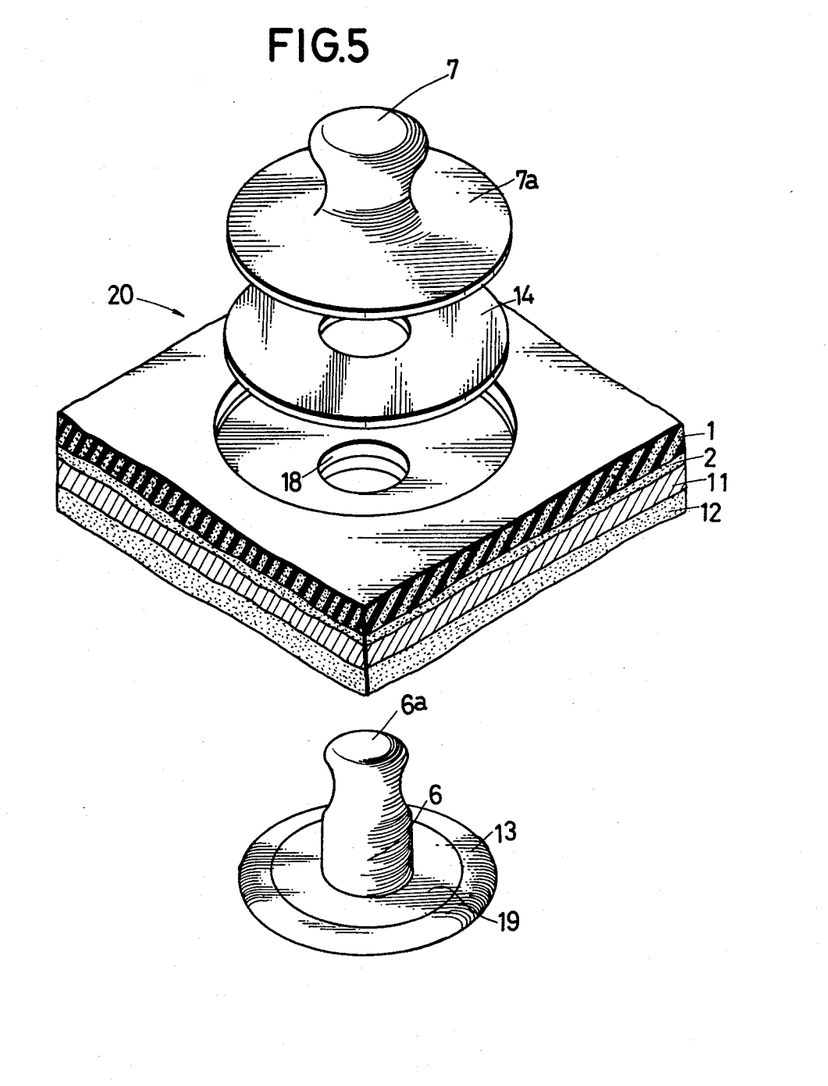
FIG. 5 is an exploded perspective view of the several elements of the electrode shown in FIG. 2.

FIG. 5 illustrates the relation of the components of electrode 20 just prior to assembly. The contacting portions including the conductive substrate 11 and the adhesive layer 12 are separately manufactured as described below. The eyelet-like elements 6 and 7 are disposed to penetrate the substrate 11 and adhesive layer 12 through the hole 18 with the solder washer 14 disposed therebetween.

When, as described above, the solder layer 14 is tightly united with upper electrode element 7 while being partly impregnated in the conductive substrate 11 to effectively contact the conductive fibers contained in the latter, the upper electrode element 7 can be electrically well connected with the conductive substrate 11. As a result, a sufficient electrical contact can be obtained and the electric resistance of the electrode can be reduced to effectively prevent the concentration of electric current.

In the conventional electrode of FIG. 1, the elements 6 and 7 are held in assembled relation only by crimping at 8, whereas, in the electrode 20 according to this invention, the elements 6 and 7, in addition to being crimped together, are soldered to the conductive substrate 11 to provide a stable attachment to the latter and superior mechanical strength.

It is preferable that the lower electrode element 6 have the ring-shaped flange 6b at the end which is to face forward the living body and that the separate washer 19 of metal be disposed between the flange 6b and the conductive adhesive 12 to prevent detachment or deviation of the lower electrode element 6 in respect to the conductive substrate. The flange 6b of element 6 can be provided with the insulating cap 13 engaging therearound or with an insulating film as fixed thereon by an adhesive, to prevent concentrations of electric currents to the living body.

In the electrode 20 of FIG. 2, the sponge-like substrate 1, which may consist of an insulating material, is affixed by adhesive layer 2 to conductive substrate 11, at the side of the latter opposite the adhesive layer 12. The lead wire or grounding cable 15 is attached through terminal plate 16 to the upper electrode element 7 to form with solder layer 14 a means for electrical connection to the conductive substrate 11. The electrode 20 of FIG. 2 is also shown to have a stripable piece of sanitary paper 17 affixed by adhesive layer 12 to the surface of the latter for maintaining the contact area of the adhesive layer 12 in a sanitary condition. The paper 17 is normally removed just prior to application of the electrode element to the surface area of the living body to be contacted.

As previously mentioned, the conductive substrate 11 of the electrode 20 according to the present invention is of a textile containing conductive fibers. Such conductive substrate may be a textile formed only of carbon fibers or only of metal fibers, for example, of copper, silver, stainless steel or the like. The conductive substrate can be constituted by a textile formed of a mixture of metal fibers and organic fibers, or a mixture of metal fibers and insulating inorganic fibers, such as, glass fibers. In the latter case, warp and woof of the textile may be woven by turns. In either case, it is preferable that at least 15% by weight, and most desirably, at least 20%, by weight, of the textile is formed of conductive fibers. When the textile forming the conductive substrate is of a mixture of fibers, the conductive fibers should uniformly appear on a surface of the respective yarn. The conductive fibers are accordingly distributed almost uniformly on a surface of the textile so that the specific resistance of the textile becomes uniform. With such construction it has been found that the conductive substrate 11 can be made to have a specific resistance, or resistivity of less than 100Ω cm.

In addition, it is preferable that the conductive substrate 11 have a thickness of 50 to 1000 μm., with a thickness of approximately 500 μm, being most preferred. The lower limit ensures that the conductive substrate will have sufficient tensile strength and the upper limit is determined to provide sufficient flexibility for conforming to the various curved surfaces found on a living body.

In one specific embodiment of the invention, conductive substrate 11 comprises a mixed textile of 20% metal fibers of stainless steel and 80% polyester fibers and has a tensile strength of 150 kg, a cutting extensibility of no more than 32%, a shrinkage percentage of 0.5% and a crease-proof precentage of more than 79%, all in the longitudinal direction of its weave. Such substrate 11 also has a tensile strength of 68 kg, a cutting extensibility of no more than 33%, a shrinkage percentage of 0% and a crease-proof percentage of more than 83%, in the lateral direction of the weave. The specific resistance of such a substrate is, for example, 60Ω cm. The metal fibers of the substrate are, for example, 8 μm in diameter. When the diameter of the metal fiber is too large, the yarns of the mixed textile tend to be hardened and the flexibility of the textile is deteriorated.

As previously mentioned, the adhesive layer 12 of electrode 20 according to the present invention contains carbon fibers, with such carbon fibers being entwined to contact each other and also appear on the surface of the layer 12. As a result, an electric resistance of the adhesive layer 12 can be relatively low and uniform. It is preferable that the carbon fibers contained in the adhesive layer 12 have a length of 0.2 to 6 mm. When the length of the carbon fibers is less than 0.2 mm, the interconnection effect resulting from the entwining of the carbon fibers is poorer. When the length of the carbon fibers is over 6 mm, the carbon fibers cannot be well dispersed in the resin and the adhesive cannot be well coated on the substrate 11. It is preferable that the diameter of the carbon fibers be 1 to 20 μm, because the conductivity is poorer when the diameter is less than 1 μm, and the dispersion of the carbon fibers in the resin and the coating property of the adhesive on the substrate are degraded when the diameter is over 20 μm. In addition, it is preferable that the content of the carbon fibers in the adhesive layer 12 be 2 to 30%, by weight, relative to the amount of the resin in the adhesive layer because the conductivity is poorer when the carbon fiber content is less than 2%, and the adhesive force of the adhesive layer is degraded due to decrease of the proportion of the resin when the carbon fiber content is over 30%. It is necessary that the conductive adhesive layer 12 have a specific resistance of no more than 100Ω cm. By way of example, when carbon fibers having a diameter of 7 μm are used, it is particularly preferable that 3% by weight of the carbon fibers be used if the latter have a length of 6 mm, that 5% by weight of the carbon fibers be used if the latter have a length of 3 mm., that 7.5 to 10% by weight of the carbon fibers be used if the latter have a length of 1 mm., and that 25% by weight of the carbon fibers be used if the latter have a length of 0.5 mm.

The adhesive layer 12 preferably has a thickness of more than 25 μm to ensure that the adhesive force will have a desired value. The thickness of the adhesive layer, in practice, is up to 200 μm, and is preferably around 100 μm. This upper limit is required from the point of view of mechanical strength of the adhesive layer in use.

To form the adhesive layer 12, a cross-linking agent may be dissolved into a diluent and a base polymer, as the resin part, is mixed into the resulting solution. As a result, the base polymer is partly cross-linked by the cross-linking agent. Carbon fibers are then dispersed into the solution of the cross-linked base polymer. The solution having the dispersed carbon fibers is uniformly coated on a paper capable of being peeled off and the solvent of the solution is evaporated. At this time, uncross-linked portions of the base polymer are cross-linked so that an almost completely cross-linked adhesive resin layer containing the carbon fibers is obtained. The previously described conductive substrate 11 is then laminated on the adhesive resin layer 12. The laminated sheet comprising the adhesive resin layer 12 and the conductive substrate 11 is then cut in a die press to produce an electrode 20 having a given size and shape.

The base polymer of the resin forming adhesive layer 12 in the electrode 20 according to the present invention will be now explained. It is preferable that a major part of the monomers of the base polymer consist of acrylic acid esters or methacrylic acid esters of an alcohol having 1 to 8 carbon atoms in its molecule, and a minor part of the monomers consist of vinyl compounds having a crosslinkable functional group.

Examples of the above acrylic acid esters are methyl acrylate, ethyl acrylate, n-propyl acrylate, isopropyl acrylate, n-butyl acrylate, tertiary butyl acrylate, amyl acrylate, n-hexyl acrylate, cyclohexyl acrylate, 2-ethyl hexyl acrylate and the like. Examples of the above methacrylic acid esters are methyl methacrylate, ethyl methacrylate, n-propyl methacrylate, n-butyl methacrylate, n-amyl methacrylate, 3-methyl-pentyl methacrylate, n-hexyl methacrylate, 2-methyl hexyl methacrylate, 2-ethyl hexyl methacrylate, n-heptyl methacrylate, n-octyl methacrylate and the like.

A portion of the acrylic or methacrylic acid ester of an alcohol having 1 to 8 carbon atoms may be substituted by another kind of vinyl compound, such as, acrylic or methacrylic acid ester having 9 to 18 carbon atoms, vinyl chloride, vinyl propionate, acrylonitrile or vinyl acetate. In such case, less than 20 parts, by weight, and preferably less than 10 parts, by weight, for each 100 parts, by weight, of the acrylic or methacrylic acid ester of alcohol of 1 to 8 carbon atoms may be replaced or substituted by the other kind of vinyl compound.

The vinyl compound having a crosslinkable functional group must be copolymerized in the base polymer in the range of 0.25 to 3.0 parts, by weight, for each 100 parts by weight of the total amount of the base polymer. The crosslinkable functional group of the vinyl compound (monomer) may be a carboxyl group, hydroxyl group, amino group, amido group or epoxy group. Examples of these vinyl compounds are acrylic acid, methacrylic acid, crotonic acid, maleic acid, itaconic acid 2-hydroxyethylacrylate, 2-hydroxypropylacrylate, 2-hydroxyethylmethacrylate, 2-hydroxypropylmethacrylate, acrylamide, methacrylamide, N-methylolacrylamide, N-mehtylolmethacrylamide, glycidylacrylate and glycidylmethacrylate.

When the base polymer is produced by copolymerization with less than 0.25 parts by weight of the crosslinkable monomer, an electroconductive pressure-sensitive adhesive layer comprising such a base polymer has an undesired low mechanical strength. On the other hand, a base polymer with more than 3.0 parts by weight of the crosslinkable monomer is apt to gelantinize and therefore is not suitable for being coated on the substrate. The base polymer suitable for the present invention has a glass transition temperature in the range from −85° to 0° C. and has an average molecular weight in the range from 50,000 to 500,000, from the point of view of pressure-sensitive adhesivity.

The base polymer used for the present invention can be synthesized by any one of the following four methods:

According to the first method, 70 parts by weight of 2-ethylhexylacrylate, 30 parts by weight of n-butylacrylate, 2.5 parts by weight of acrylic acid and 0.5 parts by weight of azobisisobutyronitrile (a polymerization initiator) are respectively dissolved into ethyl acetate (a polymerization solvent). In this case, the ratio of the polymerizable constituents and the polymerization initiator to the polymerization solvent is 1:1. The polymerizable constituents are then polymerized at a polymerization temperature of 50° to 60° C. for 8 hours. The resulting polymer is diluted by adding toluene (a diluent) to obtain a base polymer solution having a viscosity of 3925 cps.

In accordance with the second method, in which the same kinds and amounts of polymerization constitutents and polymerization initiator are used as in the first method, except 1.0 parts by weight of glycidylmethacrylate are used in place of acrylic acid for polymerization under the same conditions and a base polymer solution having a viscosity of 750 cps is obtained after the dilution of the polymer.

In the third method, in which the same kinds and amounts of polymerization constituents and polymerization initiator are used as in the first method, except 3.1 parts be weight of β-hydroxylethylmethacrylate are used in place of acrylic acid for polymerization under the same conditions, and a base polymer solution having a viscosity of 900 cps is obtained after the dilution of the polymer.

In the fourth method, 70 parts by weight of 2-ethylhexylacrylate, 70 parts by weight of n-butylacrylate, 2.5 parts by weight of acrylic acid and 0.3 parts by weight of glycidylmethacrylate are used as polymerization constituents. These constituents are polymerized by the use of 0.5 parts by weight of azobisisobutyronitrile under the same conditions as in the first method. The base polymer solution thus obtained has a viscosity of 1350 cps after the dilution of the polymer.

The base polymer produced by any one of the above methods is cross-linked by a cross-linking agent to form adhesives having a desired adhesive force. The cross-linking agent can be Tyzor A.A. (titanium chelate compound of acetyl acetone) manufactured by E. I. Du Pont Corp., ALCH (ehtyl acetate aluminum diisopropoxide), chelate compound of phenol resin and MgO and the like. The cross-linking agent reacts with the crosslinkable functional group of the base polymer, such as, the carboxyl group of acrylic acid, oxirane (ethylene oxide) group of glycidylmethacrylate and hydroxyl group of β-hydroxyethylmethacrylate. The solution of Tyzor A.A. as a cross-linking agent with a concentration of 1% is preferably used at a rate of 0.25 to 20.0 parts by weight relative to 25 parts by weight of the base polymer. The solution of ALCH as a cross-linking agent with a concentration of 1% is preferably used at a rate of about 2.0 parts by weight relative to 25 parts by weight of the base polymer. MgO chelate is preferably used at a rate of 0.25 to 1.0 parts by weight relative to 100 parts by weight of the base polymer. If the amount of the respective cross-linking agent is out of the previously indicated range therefor, that is, when the amount is too little, the thermal creep of the base polymer is deteriorated and, when the amount is too much, the base polymer is liable to gelatinize. When the cross-linking agent is used in a suitable amount, the thermal creep is more than 120 minutes and is remarkably improved in comparison with the thermal creep of a few seconds which is encountered without using a cross-linking agent.

The adhesive used in the conductive adhesive layer 12 of the present invention can be a natural rubber rather than the above-described adhesive resin comprising acrylic polymer and cross-linking agent. For example, 100 parts by weight of natural rubber of pale crepe which has been sufficiently masticated by an open roll may be dissolved into 500 weight parts of toluene. The resulting solution then has added thereto 90 parts by weight of zinc oxide, 50 parts by weight of polyisoprene (Picopal 100 SF manufactured by Esso Standard Petroleum Corp.), 24 parts by weight of carbon fibers having a diameter of 7 μm and a length of about 1 mm(Torayca manufactured by Toyo Rayon Corp.) which is produced by burning acrylonitrile fibers to carbonize and then subjecting the carbonized fibers to a heat treatment to graphitize.

Figure 7:
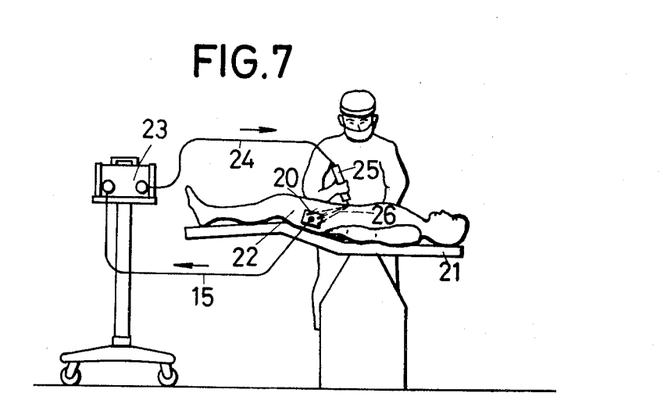
FIG. 7 is a front elevational view showing the manner in which the electrode of FIG. 2 may be used.

The electrode 20 embodying this invention may be used in the manner shown on FIG. 7. More particularly, the electrode 20 may be fixed on the thigh or back of a patient 22 on an operating table 21 and the grounding cable 15 from the electrode 20 is led to an electric surgical unit 23. An active surgical electrode 25, or electrosurgical pencil with blade, is connected to the end of an active cable 24 extending from the unit 23 and is held by a surgeon. The active surgical electrode 25 is applied to the affected part of the patient. In such a condition, high-frequency electric currents 26 are supplied to the active surgical electrode 25 by the cable 24 and then led to the electrode 20 through the body of the patient. The high-frequency electric currents serve to cut the affected part by burning and/or to effect coagulation of the blood. In addition to the above, the electrode of the present invention may also be used in connection with the making of electro-cardiogram and brain wave measurements. The small size permitted by the construction according to this invention is particularly well suited to the latter of these additional uses.

It will be evident that various modifications can be made to the above-described embodiments without departing from the scope of the present invention. For example, the lower eyelet electrode element 6 may be formed of an insulating material which acts only as a supporting member for the upper electrode element 7. The electrode elements 6 and 7 can be united by means other than the illustrated grommet construction. The lower electrode element 6 may not be formed with the flanged end 6b before being inserted through the hole 18. In other words, after the lower electrode element 6 is inserted through the hole 18 to be united with the upper electrode element 7 by crimping the lower end of lower electrode element 6 can be bent outwards against the adhesive layer 12 to form a ring-shaped portion like the flanged end 6b.

The electrical characteristics of an electrode according to the present invention will now be described in relation to FIGS. 3 and 4.

Figure 3:
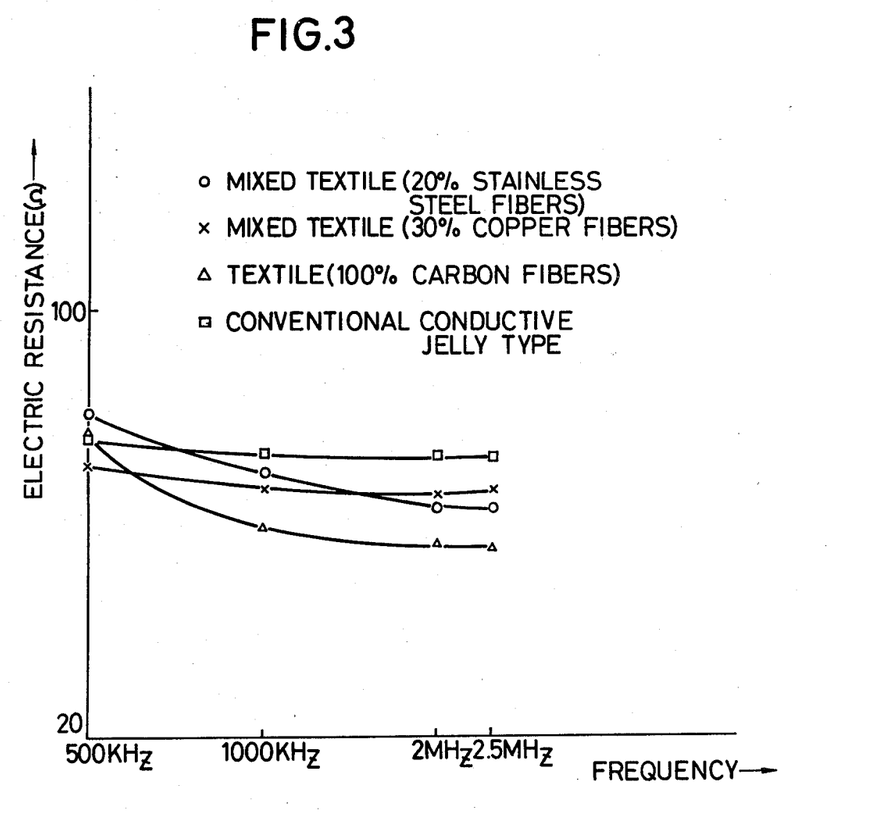
FIG. 3 is a graph showing the frequency characteristics of electrodes of the kind shown on FIG. 2 with various conductive substrates.

FIG. 3 shows the frequency characteristics of electrodes according to the present invention in comparison with the conventional conductive jelly type of electrode manufactured by American Hospital Supply Corp., with each electric resistance value for a contacting area of 10 cm×10 cm being shown for each electrode. In FIG. 3, symbols "O" show the characteristic of an electode according to the present invention in which the conductive substrate 11 is composed of a mixed textile containing 20% stainless steel fibers, the symbols "X" show the characteristic of another electrode according to the present invention in which the conductive substrate 11 is composed of a mixed textile containing 30% copper fibers, the symbols "Δ" show the characteristic of a further electrode according to the present invention in which the conductive substrate 11 is composed of a textile of 100% carbon fibers, and the symbols "□" show the characterisitic of the conventional electrode of the conductive jelly type. From FIG. 3 it will be seen that the electrodes of the present invention have a sufficiently low electric resistance of less than 100Ω, for example, in the range of 500 KHz to 25 MHz, which is a practical frequency range for an electric surgical knife, and that the resistance values of the electrodes according to the present invention are lower than or substantially equal to an electric resistance value of the conventional electrode. The electrodes according to the present invention represented on FIG. 3 each have the conductive adhesive layer 12 thereof produced by cross-linking 25 parts by weight of acrylic polymer obtained in the above described first synthesizing method by 40 parts by weight of the cross-linking agent (Tyzor A.A.) with a concentration of 1%, and adding 10% by weight of the carbon fibers having a length of 1 mm and a diameter of 7 μm to the resulting cross-linked polymer.

Figure 4A:
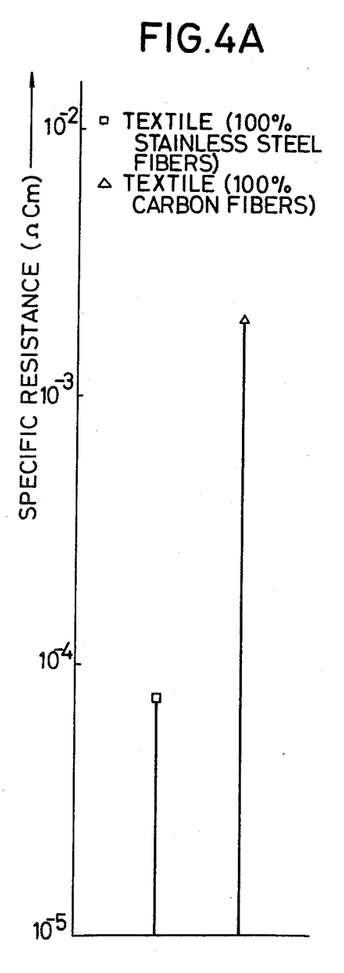
FIGS. 4A and FIG. 4B are graphs showing the specific resistance for several conductive substrates used in electrodes according to this invention.
Figure 4B:
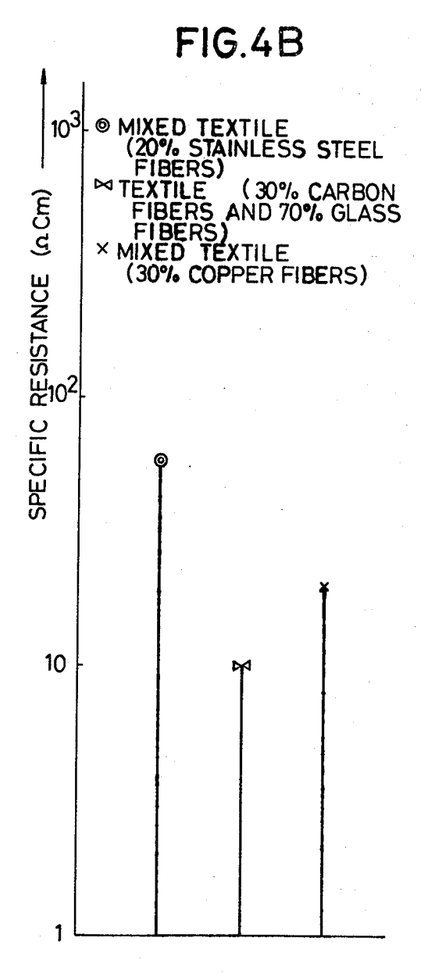

FIGS. 4A and 4B show the specific resistances or resistivities for various conductive substrates 11 that may be included in electrodes according to this invention. On FIG. 4A, the symbol "□" shows the specific resistance of a conductive substrate composed of 100% stainless steel fibers, and the symbol "Δ" shows the specific resistance of another conductive substrate composed of 100% carbon fibers. On FIG. 4B, the symbol "◎" shows the specific resistance of a conductive substrate composed of a mixed textile containing 20% stainless steel fibers, the symbol "⋈" shows the specific resistance of a conductive substrate composed of a textile comprising 30% carbon fibers and b 70% glass fibers, and the symbol "X" shows the specific resistance of a conductive substrate composed of a mixed textile containing 30% copper fibers. FIGS. 4A and 4B show that each conductive substrate according to the present invention has a specific resistance equal to or less than 100Ω cm. which is required for an electrode to be used as a grounding pad in association with an electric surgical knife. It is particularly preferable that the conductive substrate 11 be composed of a textile of 100% stainless steel fibers or 100% carbon fibers, as such conductive substrates have the lowest specific resistance values.

It will be apparent that, in the above described embodiments of the present invention, electrodes are provided with reduced electrical resistance to effectively prevent a local concentration of electric current. Also, the conductive substrate 11 and the ring-like solder layer 14 act to evenly distribute the current across the surface area of the adhesive layer 12. Additionally, the insulating cap 13 serves to insulate the lower electrode element 6 from the living body and thereby prevent concentrations of current flow therebetween. Another advantage of electrodes constructed according to the present invention is a sufficient flexibility to conform to the various concave and convex surfaces found on a living body. With such flexibility, an electrode according to the present invention can be contacted with the living body without forming any wrinkles in the electrode. Another advantage of the present invention is that the conductive substrate and adhesive layer are not dried like the gauze or jelly used in conventional electrodes, thereby preventing this cause of current concentration and the related danger of burns. In addition, the electrode according to the present invention can be easily constructed and handled from the view point of sanitization and further can be easily miniaturized, because the conductive adhesive layer 12 is integrally formed with the conductive substrate 11. An additional advantage of electrodes according to the present invention is that the same may be constructed with a mechanical strength superior to that of conventional electrodes.

Although illustrative embodiments of the invention have been described in detail herein with reference to the accompanying drawings, it is to be understood that the invention is not limited to those precise embodiments, and that various changes and modifications may be effected therein by one skilled in the art without departing from the scope or spirit of the invention as defined in the appended claims.

We claim:

1. An electrode for electrically contacting a surface of a living body comprising:

a conductive substrate of a textile having conductive fibers constituting more than 15% by weight of said textile;

a conductive adhesive layer for contacting the surface, said adhesive layer being affixed to said conductive substrate and including a mixture of carbon fibers and a resin in which said carbon fibers have a length of 0.2 to 6 mm and a diameter of 1 to 20 μm, and are contained in said adhesive layer in an amount ranging from about 2 to 30% by weight relative to the remainder of said adhesive layer;

each of said substrate and said adhesive layer having a specific resistance of less that 100Ω cm; and means forming an electrical connection to said conductive substrate.

2. An electrode according to claim 1; wherein said conductive substrate includes carbon fibers.

3. An electrode according to claim 1; wherein said conductive substrate includes conductive metal fibers.

4. An electrode according to claim 1; wherein said conductive substrate has a thickness of approximately 50 to 1000 μm and said adhesive layer has a thickness of approximately 25 to 200 μm.

5. An electrode according to claim 1; wherein said resin in the adhesive layer has a base polymer a major part of which consists of an acrylic or methacrylic acid ester of an alcohol having 1 to 8 carbon atoms in its molecule, and a minor part of the base polymer of said resin consists of a first vinyl compound having a cross-linkable functional group.

6. An electrode according to claim 5; wherein said acrylic or methacrylic acid ester is substituted by a second vinyl compound in an amount of less than 20 parts by weight of said second vinyl compound for each 100 parts by weight of said acrylic or methacrylic acid ester.

7. An electrode according to claim 6; wherein the first and second vinyl compounds are copolymerized in the base polymer in the range of 0.25 to 3.0 parts by weight of said vinyl compounds for each 100 parts by weight of the total amount of said base polymer.

8. An electrode according to claim 5; wherein said base polymer has a glass transition temperature of $-85°$ to $0°$ C. and an average molecular weight of 50,000 to 500,000.

9. An electrode according to claim 5; wherein said base polymer is cross-linked by a cross-linking agent to produce said adhesive layer.

10. An electrode according to claim 1; wherein said adhesive layer includes natural rubber.

11. An electrode according to claim 1; wherein said means for forming an electrical connection includes a cylindrical member having a flanged end and penetrating said adhesive layer and said substrate with said flanged end being against said adhesive layer, and an interconnection member affixed to the other end of said cylindrical member and being in electrical contact with said conductive substrate.

12. An electrode according to claim 11; wherein said interconnection member is soldered to said conductive substrate.

13. An electrode according to claim 11; wherein said interconnection member is crimped on, and thereby affixed to said cylindrical member.

14. An electrode according to claim 11; wherein said flanged end of said cylindrical member has an insulated cover thereon to prevent electrical contact of said cylindrical member with said surface.

15. An electrode according to claim 11; further comprising a flexible insulating material affixed to said conductive substrate on the side of said substrate opposite said adhesive layer.

* * * * *